United States Patent [19]

Kluesener et al.

[11] Patent Number: 5,142,071
[45] Date of Patent: Aug. 25, 1992

[54] SELECTIVE ESTERIFICATION OF LONG CHAIN FATTY ACID MONOGLYCERIDES WITH MEDIUM CHAIN FATTY ACIDS

[75] Inventors: Bernard W. Kluesener, Harrison; Gordon K. Stipp; David K. Yang, both of Cincinnati, all of Ohio

[73] Assignee: The Procter & Gamble Company, Cincinnati, Ohio

[21] Appl. No.: 452,877

[22] Filed: Dec. 19, 1989

[51] Int. Cl.⁵ .............................. C11C 3/08
[52] U.S. Cl. ................................. 554/172
[58] Field of Search ............ 260/410.7, 410.8

[56] References Cited

U.S. PATENT DOCUMENTS 4,747,969 5/1988 Rupilius et al. ............... 260/415

FOREIGN PATENT DOCUMENTS 64-19042 1/1989 Japan .
WO91/03944 4/1991 PCT Int'l Appl. .

OTHER PUBLICATIONS

Chemical Abstracts, vol. 111, p. 151, 1989 156414j.
Chemical Abstracts, vol. 111, p. 592, 1989, 172674z.

*Primary Examiner*—Jose G. Dees
*Assistant Examiner*—Deborah D. Carr
*Attorney, Agent, or Firm*—Richard C. Witte; Ronald L. Hemingway; Eric W. Guttag

[57] ABSTRACT

A process for the selective esterification of long chain length fatty acid monoglycerides, particularly monobehenin, with medium chain length fatty acids, particularly a mixture of $C_8$ and $C_{10}$ saturated fatty acids, is disclosed. In this process, an at least about 60% pure $C_{18}$–$C_{24}$ fatty acid monoglyceride or mixture thereof is esterified with an at least about 90% pure $C_6$–$C_{10}$ fatty acid or mixture thereof at a temperature of from about 140° to about 250° C. in the substantial absence of an esterification catalyst. The mole ratio of fatty acid to monoglyceride used in this monoglyceride esterification is at least about 3:1. Water generated during this monoglyceride esterification is also continuously removed.

34 Claims, No Drawings

5,142,071

SELECTIVE ESTERIFICATION OF LONG CHAIN FATTY ACID MONOGLYCERIDES WITH MEDIUM CHAIN FATTY ACIDS

TECHNICAL FIELD

This application relates to a process for the selective esterification of long chain length fatty acid monoglycerides with medium chain length fatty acids to provide reduced calorie fats. This application particularly relates to the esterification of monobehenin with a mixture of $C_8$ and $C_{10}$ saturated fatty acids to provide a preferred reduced calorie confectionary fat.

European patent application 322,027 to Sieden, published Jun. 28, 1989, discloses reduced calorie fats comprising triglycerides having medium chain length ($C_6$–$C_{10}$) saturated fatty acid residues and long chain length (e.g., $C_{18}$–$C_{24}$) saturated fatty acid residues. These reduced calorie fats primarily comprise triglycerides selected from mono- long chain length MLM and MML triglycerides, and di- long chain length LLM and LML triglycerides, where M is a medium chain saturated fatty acid residue(s) and L is a long chain saturated fatty acid residue(s). These reduced calorie fats can be used as complete or partial replacements for other triglycerides fats to provide calorie reduction in various fat-containing food compositions such as salad oils, emulsified spreads, frozen desserts and the like.

For certain preferred reduced calorie fats, L is predominantly a long chain behenic fatty acid residue and M is a mixture of $C_8$ and $C_{10}$ saturated fatty acids. These preferred reduced calorie fats are useful as partial or complete replacements for confectionary fats, especially cocoa butter, particularly in chocolate-flavored products such as candy bars and enrobed chocolate-flavored products. To provide optimum mouthmelt properties for these preferred reduced calorie fats, the level of MML and MLM (mono-long chain) triglycerides combined is desirably maintained, e.g., to levels of about 90% or higher.

This European patent application 322,027 described the synthesis of these reduced calorie fats by a wide variety of techniques. These techniques include: (a) random rearrangement of long chain triglycerides (e.g., tristearin or tribehnin) and medium chain triglycerides; (b) esterification of glycerol with a blend of the corresponding fatty acids; (c) transesterification of a blend of medium and long chain fatty acid methyl esters with glycerol; and (d) transesterification of long chain fatty acid glycerol esters (e.g., glyceryl behenate) with medium chain triglycerides. In particular, Example 1 of European patent application 322,027 discloses the synthesis of such reduced calorie fats by random rearrangement of tribehenin and commercial grade medium chain triglycerides using sodium methoxide as the catalyst at reaction temperatures of from 78° to 91° C. This catalyzed random rearrangement synthesis provides a complex mixture of MLM, MML, LML, LLM, MMM and LLL triglycerides, as well as the various mono- and diglycerides. (A similar, complex mixture of triglycerides is obtained when glycerol is esterified with a mixture of medium and long chain fatty acids, in the absence of an esterification catalyst, at temperatures of about 265° C.) Of this complex mixture, the particularly desirable MML/MLM triglycerides comprise, at most, only about 40 to about 45% of the total triglycerides. This necessitates an extensive purification step by techniques such as molecular distillation, solvent fractional crystallization, winterization, or a combination of such techniques, to increase the level of desired MML/MLM triglycerides in the reduced calorie fat.

Menz, ""Polymorphism of Diacid Triglycerides of the Stearic Acid and Behenic Acid Series," *Fette Seifen Anstrichmittel*, Vol. 77, Issue 5 (1975), pp. 170–73, discloses the selective esterification of 1-monostearin and 1-monobehenin with short/medium chain ($C_2$–$C_8$) saturated fatty acid chlorides in pyridine. See also Jackson et al, "The Polymorphism of 1-Stearyl and 1-Palmityl-Diacetin, -Dibutyrin-Dicaproin and 1-Stearyl Dipropionin," *J. Am. Chem. Soc.*, Vol. 73(1951), pp. 4827–29, which discloses the selective esterification of 1-monostearin or 1-monopalmitin with the respective fatty acid chlorides of acetic acid, butyric acid or caproic acid. The fatty acid chlorides used in the Menz and Jackson et al processes are extremely expensive, particularly in synthesizing MML/MLM triglycerides on a commercial scale. In addition, these fatty acid chlorides are extremely toxic and generate undesirable reaction by-products during esterification that need to be removed prior to use of the MML/MLM triglycerides in food applications. Accordingly, it would be desirable to have a process for selectively obtaining MML/MLM triglycerides which uses less expensive and nontoxic acylating materials that eliminate the generation of by-products known to be undesirably, without the use of esterification catalysts or solvents.

BACKGROUND ART

A. Random Rearrangement of Tribehenin and Medium Chain Triglycerides

European patent application 322,027 to Seiden, published Jun. 28, 1989, discloses the preparation of a complex mixture of MML, MLM, LML, MLL, LLL and MMM triglycerides by random rearrangement of tribehenin and commercial grade medium chain triglycerides using sodium methoxide as the catalyst at reaction temperatures of from 78–91° C. See Example 1.

B. Esterification of 1-Monobehenin and 1-Monostearin with Short/Medium Chain Acid Chlorides Menz, "Polymorphism of Diacid Triglycerides of the Stearic Acid and Behenic Acid Series," *Fette Seifen Anstrichmittel*, Vol. 77, Issue 5 (1975), pp. 170–73, discloses a study of the polymorphic properties of 1-monostearin and 1-monobehenin which have been esterified with $C_2$, $C_4$, $C_6$ or $C_8$ short/medium chain saturated fatty acid chlorides in pyridine.

Jackson et al, "The Polymorphism of 1-Stearyl and 1-Palmityl-Diacetin, -Dibutyrin-Dicaproin and 1-Stearyl Dipropionin," *J. Am. Chem. Soc.*, Vol. 73 (1951), pp. 4827–29, discloses the polymorphism of 7 unsymmetrical triglycerides obtained by esterifying 1-monostearin or 1-monopalmitin with the respective fatty acid chlorides of acetic acid, butyric acid or caproic acid. See also Feuge et al, "Dilatometric Properties of Some Butyropalmitins, Butyrostearins, and Acetopalmitins," *J. Am. Oil Chem. Soc.*, Vol. 33, 1956, pp. 367–71, for a similar disclosure.

C. Esterification of Monostearin with Short/Medium Chain Fatty Acids

Tsuda et al, "Melting Points and Hardness of Saturated Triglycerides Containing Lower Fatty Acids", *Osaka Furitsu Kogyo Shoreikan Hokoko*, No. 25 (1961), pp. 44–48 (Chem. Abstracts 61:849h), discloses monostearins esterified with lower fatty acids such as acetic, propionic, isobutyric, isocaproic, caproic, caprylic, and capric acid. In these esterifications, 1, 1.2 or 2 moles of propionic, isobutyric, isocaproic, caproic, caprylic, or capric acid, were reacted with 1 mole of monostearin using stannous chloride as the catalyst, to obtain glycerides alleged to be useful as cocoa butter substitutes.

D. Controlled/Directed Esterification of 1-Monostearin Using p-Toluenesulfonic Acid as the Catalyst Feuge et al, "Preparation of Triglycerides by Controlled Esterification," *J. Am. Oil Chem. Soc.*, Vol. 40 (1963), pp. 260-65, discloses the esterification of 1-monostearin with oleic acid (10% excess) at temperatures of 100°, 120°, 150° and 200° C., using p-toluenesulfonic acid as the catalyst. This reference suggests interesterification that occurs in some acid-catalyzed esterifications is caused by water formed during the reaction, and therefore recommends its continuous removal by stripping with vaporized hexane. This 1-monostearin esterification process is taught to be useful in making tailor-made fats such as cocoa butter-like fats. See also Gros et al. Preparation of Partial Glycerides by Direct Esterification," *J. Am. Oil Chem. Soc.*, Vol. 41 (1964), pp. 727-31 (esterification of 1-monostearin with oleic, stearic or lauric acid in a 1:1 or 1:2 mole ratio at a reaction temperature of 80° or 100° C. using p-toluenesulfonic acid as the catalyst to obtain the respective diglycerides); U.S. Pat. No. 3,119,849 to Feuge et al, issued Jan. 28, 1964 (esterification of diglycerides of palmitic and/or stearic acid with oleic acid using p-toluenesulfonic acid as the catalyst with azeotropic distillation to remove generated water).

DISCLOSURE OF THE INVENTION

The present invention relates to a process for selectively making MML/MLM triglycerides that are useful as reduced calorie fats, wherein M is a $C_6$-$C_{10}$ fatty acid residue or mixture thereof, and L is a $C_{18}$-$C_{24}$ fatty acid residue or mixture thereof, and preferably MML/MLM triglycerides that are useful as reduced calorie confectionery fats, wherein M is a mixture of $C_8$ and $C_{10}$ saturated fatty acid residues, and L is at least about 90% behenic fatty acid residues. In this process, an at least about 60% pure $C_{18}$-$C_{24}$ fatty acid monoglyceride or mixture thereof is esterified with an at least about 90% pure $C_6$-$C_{10}$ fatty acid or mixture thereof at a temperature of from about 140° to about 250° C. in the substantial absence of an esterification catalyst. The mole ratio of fatty acid to monoglyceride used in this monoglyceride esterification is at least about 3:1. Water generated during this monoglyceride esterification is also continuously removed.

The monoglyceride esterification process of the present invention has a number of significant advantages over prior random rearrangement synthesis processes and acid chloride esterification processes. The monoglyceride esterification process of the present invention is relatively fast and is high selective in obtaining MML/MLM triglycerides, e.g. with purities as high as from about 80 to about 96% (after unreacted fatty acids are removed), if the monoglyceride is added slowly to the melted fatty acids. As a result, the subsequent purification step to further increase the level of MML/MLM triglycerides is not as extensive, and may not even be required in certain cases. In addition, the monoglyceride esterification process of the present invention uses significantly less expensive and nontoxic free fatty acid starting materials that eliminate the generation of known, undesired by-products, such as difatty ketones. Esterification catalysts and solvents are also not required, or even desired, in the process of the present invention. Furthermore, the esterification process of the present invention typically goes essentially to completion (i.e. at least 99% of the partial glycerides are converted to triglycerides), which is difficult to achieve in prior esterification reactions involving fatty acids and glycerol.

A. Definitions

By "medium chain fatty acid," as used herein, is meant a saturated fatty acid, unsaturated fatty acid, or mixture thereof, having 6 to 10 carbon atoms.

By "medium cain saturated fatty acid," as used herein, is meant $C_6$ (caproic), $C_8$ (caprylic, or $C_{10}$ (capric) saturated fatty acids, or mixtures thereof. The $C_7$ and $C_9$ saturated fatty acids are not commonly found, but they are not excluded from the possible medium chain fatty acids. The present medium chain fatty acids do not include lauric acid ($C_{12}$), sometimes referred to in the art as a medium chain fatty acid.

By "long chain fatty acid," as used herein, is meant a saturated fatty acid, unsaturated fatty acid, or mixture thereof, having 18 to 24 carbon atoms.

By "long chain saturated fatty acid," as used herein is meant $C_{18}$ (stearic), $C_{19}$ (nonadecyclic), $C_{20}$ (arachidic), $C_{21}$ (heneicosanoic), $C_{22}$ (behenic), $C_{23}$ (tricosanoic), or $C_{24}$ (lignoceric) saturated fatty acids, or mixtures thereof.

By "MML," as used herein, is meant to triglyceride containing a long chain fatty acid residue in the #1 or #3 position (an end position) with two medium chain fatty acid residues in the remaining two positions, while "MLM" represents a triglyceride with a long chain fatty acid residue in the #2 position (the middle position) and two medium chain fatty acid residues in the #1 and #3 positions. Similarly, "MLL" represents a triglyceride with a medium chain fatty acid residue in the #1 or #3 position and two long chain fatty acid residues in the remaining two positions, "LML" represents a triglyceride with a medium chain fatty acid residue in the #2 position and two long chain fatty acid residues in the #1 and #3 positions, "MMM" represents a triglyceride containing medium chain fatty acid residues at all three positions, and "LLL" represents a triglyceride containing long chain fatty acid residues at all three positions.

By "the level of MML/MLM triglycerides" is meant the combined level of MML and MLM triglycerides.

By "long chain fatty acid monoglyceride" is meant a monoglyceride which contains one long chain fatty acid residue in the #1 position (i.e., a 1-monoglyceride or the #2 position (i.e., a 2-monoglyceride).

As used herein, the term "comprising" means various components or steps can be conjointly employed in the present invention. Accordingly, the term "comprising" encompasses the more restrictive terms "consisting essentially of" and "consisting of."

All percentages, ratios and proportions used herein are by weight unless otherwise specified.

B. Sources of Medium Chain Fatty Acids

The medium chain (i.e., $C_6$-$C_{10}$) fatty acids useful in the monoglyceride esterification process of the present invention can be derived from a number of different sources. For example, medium chain saturated fatty acids can be obtained from coconut, palm kernel or babassu oils. They can also be obtained from commercial medium chain triglycerides, such as the Captex 300 brands sold by Capital City Products of Columbus, Ohio. Typically, these sources of medium chain fatty acids are subjected to hydrolysis to provide a mixture of free fatty acids, followed by solventless fractionation to provide a fatty acid fraction enriched in the medium chain fatty acids. For example, refined, bleached, and deodorized coconut or palm kernel oil, which has been hydrogenated to further increase the level of saturated fatty acids, can be subjected to hydrolysis conditions, followed by solventless fractionation (i.e. distillation) to provide a fatty acid fraction enriched in a mixture of $C_8$ and $C_{10}$ saturated fatty acids that is typically processed to meet Food Chemical Codex criteria for caprylic ($C_8$) and capric ($C_{10}$) acids. It is also desirable that the sources of medium chain fatty acids have good thermal color stability, e.g., after heating at 205° C. for 2 hours, a mixture of $C_8$ and $C_{10}$ saturated fatty acids has only a 5–10% optical transmission reduction when measured at 440/550 nanometers.

The source of medium chain fatty acids used in the monoglyceride esterification process of the present invention needs to be of sufficiently high purity to provide the desired level of MML/MLM triglycerides. Generally the source of medium chain fatty acids is at least about 90% pure in medium chain fatty acids, and is preferably at least about 95% pure, in such fatty acids. Preferably, the source of medium chain fatty acids comprises $C_8$ saturated fatty acid, $C_{10}$ saturated fatty acid, or a mixture of $C_8$ and $C_{10}$ saturated fatty acids. The weight ratio of $C_8$ to $C_{10}$ saturated fatty acids is preferably in the range of from about 30:70 to about 45:55.

C. Sources of Long Chain Fatty Acid Monoglycerides

The long chain (i.e., $C_{18}$–$C_{24}$) fatty acid monoglycerides used in the monoglyceride esterification process of the present invention can be prepared by a wide variety of techniques. These techniques include:

(a) Esterification or transesterification of glycerol acetone or glycidol with the respective long chain fatty acid(s), or long chain fatty acid lower alkyl (e.g., methyl or ethyl) ester(s), followed by hydrolysis of the respective blocking group. See Hartman, "Preparation of α-Monoglycerides by a Modified Isopropylidene-Glycerol Method," *Chemistry and Industry* (Jun. 18, 1960), pp. 711-12 (herein incorporated by reference), which discloses the preparation of 1-monoglycerides by the use of the modified isopropylidene-glycerol method, and Mattson et al, "Synthesis and Properties of Glycerides," *J. Lipid Res.*, Vol. 3, No. 3 (1962), pp. b 281-96 (herein incorporated), which discloses the same method. See also U.S. Pat. No. 3,595,888 to Reiser et al, issued Jul. 27, 1971, and U.S. Pat. No. 3,251,870 to Dalby, issued May 17, 1966 (herein incorporated by reference) which disclose isopropylidene-glycerol and glycidol methods for synthesizing monoglycerides.

(b) Esterification or transesterification of glycerol with the respective long chain fatty acid(s), or long chain fatty acid lower alkyl ester(s), optionally using strong base esterification catalysts such as sodium hyroxide or sodium methoxide, or strong acid esterification catalysts such as hydrogen fluoride, perchloric acid, phosphoric acid or p-toluenesulfonic acid. See Choudhury, "The Preparation and Purification of Monoglycerides: Direct Esterification of Fatty Acids with Glycerol", *J. Am. Oil Chem. Soc.* Vol. 39 (1962), pp. 345-47 (herein incorporated by reference), which discloses the preparation of monoglycerides by esterification of glycerol with various fatty acids (e.g. stearic acid), optionally using sodium hydroxide as the catalyst. See also U.S. Pat. No. 3,551,464 to Miller et al, issued Dec. 29, 1970 (herein incorporated by reference), which discloses the preparation of monoglycerides from long chain aliphatic acids and esters that are esterified or transesterified with glycerol using hydrogen fluoride as the catalyst.

(c) Hydrolysis of a naturally occurring oil, preferably a completely or substantially completely hydrogenated naturally occurring oil (e.g., high erucic acid rapeseed oil or soybean oil hydrogenated to an Iodine Value (I.V.) of about 10 or less) by the use of a 1,3-specific lipase, followed by removal of the residual fatty acids, glycerol, diglycerides and triglycerides. See Holmberg, "Enzymatic Preparation of Monoglycerides in Microemulsion," *J. Am. Oil Chem. Soc.*, Vol. 65 (1988), pp. 1544-48, which is incorporated by reference.

(d) Esterification of transesterification of glycerol with the respective long chain fatty acid(s) or long chain fatty acid lower alkyl ester(s) using a monoglyceride lipase (e.g., Ammano Pharmaceutical type G), followed by purification. See European patent application 191,217 to Yamaguchi et al, published Aug. 20, 1986, which is incorporated by reference.

(e) Glycerlysis of naturally occurring oils, preferably completely or substantially completely hydrogenated naturally occurring oils. See Choudhury, "The Preparation and Purification of Monoglycerides; Glycerolysis of Oils", *J. Am. Oil Chem. Soc.*, Vol. 37 (1960), pp. 483-86, and Feuge et al, "Modification of Vegetable Oils: The Practical Preparation of Mono- and Diglycerides," *Oil and Soap*, (August, 1946), pp. 259-64, which are incorporated by reference.

The long chain fatty acids per se or naturally occurring fats and oils can serve as sources of the long chain fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils. Alternatively, mixed chain length fatty acid monoglycerides can be fractionated to provide a source of long chain fatty acids. For example, hydrogenated high erucic acid rapeseed oil can be transesterified with glycerol to provide a mixture of long chain fatty acid monoglycerides which can be subsequently fractionated by liquid/liquid extraction or adsorptive separation to yield a monobehenin-enriched mixture. The source of long chain fatty acids usually needs to be of sufficiently high purity in order to provide monoglycerides suitable for the esterification process of the present invention. Usually, the source of long chain fatty acids is at least about 90% pure in long chain fatty acids, and is preferably at least about 95% pure in such fatty acids. Preferably, the purity is in the range of from about 90 to about 98% long chain fatty acids.

For the esterification process of the present invention, the source of long chain fatty acid monoglycerides needs to be of sufficiently high purity in order to provide the desired level of MML/MLM triglycerides. Generally, the source of these monoglycerides, needs to be at least about 60% pure in long chain fatty acid monoglycerides, and is preferably at least about 90% pure, most preferably at least about 95% pure, in such monoglycerides. Such purities can typically be achieved by purification of the crude source of monoglycerides by molecular distillation, fractional crystallization, liquid/liquid extraction or adsorptive separation, e.g., by weak acid ion exchange resins to remove various impurities, including unreacted long chain fatty acids and particularly, to decrease the level of dilong chain fatty acid diglycerides (LL) to about 3% or less. Residual glycerol present in the crude source of monoglycerides can be removed by settling centrifugation, thermal distillation, or fractional crystallization to decrease the glycerol level to about 1% or less. In addition, it is desirably to minimize the formation of glycerol dehydration products (e.g., polyglycerols) to a level of about 1% or less.

The preferred source of monoglycerides for use in the esterification process of the present invention is at least about 90%, and is preferably at least about 95%, pure monobehenin. This preferred monoglyceride can be obtained by hydrolysis of substantially completely hydrogenated (i.e., I.V. about 10 or less) high erucic acid rapeseed oil, solventless fractionation of the resulting fatty acid mixture to provide a behenic fatty acid-enriched fraction, and then esterification of glycerol with this behenic acid-enriched fraction to provide a crude mixture of monoglycerides. This synthesis route minimizes the formation of base catalyzed by-products such as difatty ketones or diglycerols. This crude monoglyceride mixture can be subsequently purified by molecular distillation, solvent (e.g., ethyl alcohol) crystallization, liquid/liquid extraction or adsorption on a weak acid ion exchange resin to yield a source of monoglycerides having the desired purity of monobehenin.

Esterification of Monoglycerides with Medium Chain Fatty Acids

The desired MML/MLM triglycerides are made according to the process of the present invention by the esterification of the long chain fatty acid monoglycerides described in part C of this application with the medium chain fatty acids described in part B of this application. A particularly important aspect of this esterification process is to use an excess of the medium chain fatty acids relative to the monoglycerides, i.e. a mole ratio of fatty acid to monoglyceride of at least about 3:1. Typically, the mole ratio of fatty acid to monoglyceride is in the range of from about 4:1 to about 36:1, with a preferred mole ratio in the range of from about 8:1 to about 20:1, i.e. a substantial excess. Mole ratios higher than about 27:1 can be used in this esterification process, but are usually not desirable since this results in a significant amount of unreacted fatty acid that needs to be removed during subsequent purification and does not significantly increase the level of desired MML/MLM triglycerides.

Another important aspect of the esterification process of the present invention is that it is typically carried out in a solvent-free system. At the temperatures at which the esterification process is carried out, the mixture of monoglycerides and medium chain fatty acids forms an essentially homogeneous melt. Accordingly, solvents are not required in carrying out the esterification process of the present invention.

Another important aspect of the esterification process of the present invention is that it is carried out in the substantial absence of an esterification catalyst. As used herein, the term "substantial absence of esterification catalyst" means that the esterification process of the present invention is carried out without intentionally adding such catalysts. Esterification catalysts such as strong bases (e.g. sodium hydroxide or sodium methoxide) and strong acids (e.g. phosphoric acid or p-toluenesulfonic acid) are not required in order to carry out the esterification process of the present invention. Indeed, it has been surprisingly found that strong acid esterification catalysts such as phosphoric acid or p-toluenesulfonic acid tend to promote undesired rearrangement of the resulting glycerides, thus decreasing the level of desired MML/MLM triglycerides. In addition to promoting undesired rearrangement, strong base esterification catalysts such as sodium methoxide have also been found to cause the formation of undesired di-fatty ketone by-products.

Another important aspect of the esterification process of the present invention is the esterification temperatures used. Surprisingly, it has been determined that, at esterification temperatures of about 250° C. or less, the esterification of monoglycerides with medium chain fatty acids is favored over rearrangement of the long chain fatty acid residues attached to the glyceride due to hydrolysis/reesterification. In particular, it has been observed that the medium chain fatty acids attached to the glyceride hydrolyze much faster than the long chain fatty acids at temperatures of about 25° C. or less, thereby reducing the extent of long chain fatty acid hydrolysis and subsequent reesterification (i.e. rearrangement), especially when there is a substantial excess of medium chain fatty acids relative to the monoglycerides. In other words, the esterification process of the present invention is "selective" in converting the monoglycerides to the desired MML/MLM triglycerides.

With this guideline in mind, the esterification process of the present invention can be carried out over a fairly wide range of temperatures. Generally, the esterification of the monoglycerides with the medium chain fatty acids can be carried out at a temperature in the range of from about 140° to about 250° C. Preferably, the esterification of the monoglycerides with the medium chain fatty acids is carried out at a temperature in the range of from about 180° to about 220° C. This preferred range is particularly desirable in esterifying the preferred monobehenin monoglycerides with $C_8C_{10}$ saturated fatty acids. When such temperature conditions are employed, the extent of long chain fatty acid hydrolysis is minimized, e.g., to about 2% or less. Progressively increasing temperatures during esterification are also advantageous in maximizing the level of MML/MLM triglycerides obtained.

Another important aspect of the esterification process of the present invention is the removal of water generated during the reaction of the medium chain fatty acids with the monoglycerides. It has been found that water generated during this reaction that remains in the reaction mixture can cause hydrolysis of the resulting glycerides, and therefore lead to undesired rearrangement that decreases the level of desired MML/MLM triglycerides. Accordingly, water that is generated during the reaction is continuously removed from the reaction mixture. Suitable methods for continuous removal of this generated water include vacuum stripping of the reaction mixture (e.g., at pressures of from 50 to 300 mm Hg), inert gas (e.g., nitrogen) sparging of the reaction mixture using high shear mixing with high gas velocities, adsorption by hydrophilic materials such as zeolite molecular sieves, activated carbon and activated alumina, or combinations of these techniques. For example, in the case of nitrogen gas sparging, 0.1 to 10 l./min. gas flow per liter of reaction mixture in conjunction with high shear mixing (e.g. a 5 to 600 m./min. tip speed) are preferred for removal of generated water. (This degree of high shear mixing is typically achieved by a drive motor energy input of 1.5 to 3 kilowatts per 1000 liters of reaction mixture.) In addition, it is preferred that the fatty acids and monoglyceride starting materials be essentially anhydrous (e.g. by vacuum dehydration) prior to esterification.

The esterification process of the present invention can be carried out as either a batch or continuous reaction system. For example, mixed flow configuration can be used to continuously react the medium chain fatty acids with the monoglycerides in one or more reaction stages. It is preferred that the reaction system(s) be equipped with partial condensors to allow continuous reflux of the medium chain fatty acids while generated water is being removed. Alternatively, thin film-type reaction systems operated under vacuum at high temperatures with short residence times can be used in this esterification step. Typically, the solid or liquid monoglycerides are added to the melted medium chain fatty acids at the desired esterification temperature to permit more effective removal of generated water and to minimize disproportionation of the monoglycerides to diglycerides/glycerol, as well as the reaction of monoglycerides with medium and long chain (ML) diglycerides. The monoglycerides are also preferably added slowly to the melted fatty acids at a controlled rate of addition during esterification to minimize the concentration of unreacted monoglycerides in the mixture (e.g., to about 0.2% or less), and thus minimize the formation of MLL/LML triglycerides.

The particular reaction times for carrying out this esterification process can vary greatly depending upon the mole ratio of fatty acids to monoglycerides used, the particular esterification temperatures used, and the yield/degree of purity desired for the MML/MLM triglycerides. Usually, reaction times of from about 0.1 to about 7 hours are suitable for batch reaction systems. Preferably, the esterification process of the present invention is carried out for a period of from about 1 to about 5 hours in a batch reaction system. (Equivalent residence times can be used in continuous reaction systems.)

An important result of the esterification process of the present invention is that at least 99% of the partial glycerides are converted to the respective triglycerides. In prior esterification reactions involving fatty acids and glycerol, it is difficult to achieve such conversions. For example, prior esterification reactions involving fatty acids and glycerol typically result in a residual level of diglycerides on the order of about 2 to 3%. The presence of such a high level of diglycerides can potentially cause bloom formation if the MML/MLM triglycerides are used in flavored confectionary fat products, thus requiring extensive purification such as by solvent fractionation or resin absorbents, to decrease the level of such diglycerides. By contrast, the esterification process of the present invention can achieve very low diglyceride levels, e.g. diglyceride levels of about 1% or less. This makes the MML/MLM triglycerides obtained by the esterification process of the present invention particularly suitable for flavored confectionary fat products.

E. Purification to Increase the Level of MML/MLM Triglycerides

After the esterification process described in part D of this application has been carried out for the appropriate time, the level of desired MML/MLM triglycerides in the reaction mixture is usually at least about 55%, is typically at least about 80%, and is preferably at least about 90%. The particular level of MML/MLM triglycerides present in the reaction mixture will depend upon a number of factors, including the purity of the medium chain fatty acid and monoglyceride starting materials, and the reaction conditions used. For example, the esterification of at least about 90% pure monobehenin monoglyceride with an at least 95% pure mixture of $C_8$ and $C_{10}$ saturated fatty acids in a mole ratio of fatty acids to monoglyceride in the range of from about 8:1 to about 20:1 at a reaction temperature in the range of from about 180° to about 220° C. for from about 1 to about 5 hours typically results in a reaction mixture containing a level of from about 80 to about 96% MML/MLM triglycerides.

The level of MML/MLM triglycerides in this reaction mixture can be sufficiently high so that further purification is unnecessary, particularly depending upon the proposed use of the MML/MLM triglycerides. However, purification of the reaction mixture resulting from the esterification step is typically required in order to remove various components such as unreacted medium chain fatty acids, and, in particular, MMM and MLL/LML triglycerides.

Subsequent purification can be carried out by a variety of techniques, or combinations of techniques. For example, fatty acids, such as unreacted medium chain fatty acids, present in the reaction mixture can be removed by precipitation as salts (e.g., by addition of a base such as potassium carbonate), by the use of reverse osmosis membranes (e.g., NIRO HR 98 polyamid/polysulfane thin film composite membranes) having a low (e.g., 200 molecular weight) cutoff, by flash evaporation, by steam stripping, or by vacuum distillation, to decrease the level of fatty acids in the reaction mixture to about 2% or less (as oleic acid). MMM triglycerides, and any residual fatty acids, can be removed by, for example, flash evaporation, evaporation using a wiped film evaporator (e.g., at temperatures of 200° to 240° C. and at pressures of 0.1-0.5 mm. Hg), molecular distillation (e.g., at 180°-225° C. and 1-20 microns pressure, preferably with the fatty acids/MMM triglycerides as the distillate fraction) or by fractional crystallization using acetone, ethanol, methanol or hexane as the solvent, to decrease the level of MMM triglycerides in the reaction mixture to about 3% or less and the level of residual fatty acids to about 0.5% or less (as oleic acid). MLL/LML triglycerides can be separated from the MML/MLM triglycerides by, for example, molecular distillation (e.g., at 200°-250° C. and 1-20 microns pressure, preferably with the MML/MLM triglycerides as the distillate fraction), solventless fractional crystallization (e.g., at 80° F. to promote crystal growth, followed by 70°-75° F. filtration), or solvent fractional crystallization using acetone, ethanol, methanol or hexane as the solvent, to decrease the level of combined MLL/LML triglycerides in the reaction mixture to about 3% or less. Surprisingly, the reaction mixture, which typically contains free fatty acids, is thermally stable, e.g., heating the reaction mixture for 1 hour at 240° C. does not cause significant rearrangement. Accordingly, a variety of thermal techniques can be used to purify the reaction mixture.

Any fatty acids, MMM triglycerides, MLL/LML triglycerides or diglycerides removed during purification can be recycled to provide sources of medium chain fatty acids or long chain fatty acid monoglycerides for further esterification according to the process of the present invention. Alternatively, these materials can be reincorporated into the esterification mixture at low levels for subsequent reaction to provide additional MML/MLM triglycerides. The purified mixture of MML/MLM triglycerides can also be subjected to bleaching and deodorizing steps for color and flavor-/aroma improvement using conventional techniques well known in the fats and oils art. Alternatively, the reaction mixture can be bleached using conventional bleaching earth and/or activated carbon prior to purification. In the case of MML/MLM triglycerides which have unsaturated fatty acid residues or mixtures of unsaturated and saturated fatty acid residues, the MML/MLM triglycerides can be hydrogenated, before or after purification, to convert the unsaturated fatty acid residues to saturated fatty acid residues.

F. Uses of MML/MLM Triglycerides as Reduced Calorie Fats

The MML/MLM triglycerides obtained according to the present invention (where L is a long chain saturated fatty acid residue and M is a medium chain saturated fatty acid residue) can be used as reduced calorie fats to partially or totally replace normal triglyceride fat in an fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat. On the other hand, very low calorie and thus high desirable food compositions are obtained when the total fat comprises up to 100% of the reduced calorie fat, and up to about 50% of the calories.

The present reduced calorie fats are useful in a wide variety of food and beverage products. For example, the fats can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked good, pizzas and pizza crusts, baked farinaceous snack foods, and other baked salted snacks.

In addition to their uses in baked goods, the reduced calorie fats can be used along or in combination with other regular calorie fats and oils to make shortening and oil products. Suitable sources of regular fats and oils include, but are not limited to: 1) vegetable fats and oils such as soybean, corn, sunflower, rapeseed, low erucic acid rapeseed, canola, cottonseed, olive, safflower, and sesame seed; 2) meat fats such as tallow or lard; 3) marine oils; 4) nut fats and oils such as coconut, palm, palm kernel, or peanut; 5) milkfat; 6) cocoa butter and cocoa butter substitutes such as shea, or illipe butter; and 7) synthetic fats. Shortening and oil products include, but are not limited to, shortenings, margarines, spreads, butter blends, lards, salad oils, popcorn oils, salad dressings, mayonnaise, and other edible oils.

Certain of the present reduced calorie fats are especially useful in flavored confectionary compositions, particularly chocolate-flavored confectionary compositions. See U.S. application Ser. No. 329,619 to Albert M. Ehrman, Paul Seiden, Rose M. Weitzel and Robert L. White, (P&G Case 3948), filed Mar. 28, 1989, which is incorporated by reference. These flavored confectionary compositions comprise:

a. a flavor enhancer amount of a flavor component;
b. from about 25 to about 45% of a fat component comprising:
(1) at least about 70% of a reduced calorie fat having:
(a) at least about 85% combined MLM and MML triglycerides;
(b) no more than about 5% combined LLM and LML triglycerides;
(c) no more than about 2% LLL triglycerides;
(d) no more than about 4% MMM triglycerides;
(e) no more than about 7% other triglycerides;
wherein M is a $C_6$ to $C_{10}$ saturated fatty acid residue and L is a $C_{20}$ to $C_{24}$ saturated acid residue;
(f) a fatty acid composition having:
(i) from about 40 to about 60% combined $C_8$ and $C_{10}$ saturated fatty acids,
(ii) a ratio of $C_8$ to $C_{10}$ saturated fatty acids of from about 1:2.5 to about 2.5:1,
(iii) from about 40 to about 60% behenic fatty acid,
(2) up to about 15% milkfat;
(3) up to about 20% cocoa butter;
(4) no more than about 4% diglycerides; and
c. from about 55 to about 75% other nonfat confectionery ingredients.

These compositions are preferably tempered according to the process disclosed in said Ehrman et al application which comprises the following steps:

(I) forming a temperable flavored confectionary composition as defined above;

(II) rapidly cooling the composition of step (I) to a temperature of about 57° F. or less so that the reduced calorie fat forms a sub $\alpha$ phase;

(III) holding the cooled composition of step (II) at a temperature of about 57° F. of less for a period of time sufficient to form an effective amount of $\beta$-3 crystals from a portion of the sub $\alpha$ phase of the reduced calorie fat; and (IV) after step (III), warming the cooled composition to a temperature in the range of from above about 57° to about 72° F. in a manner such that: (a) the remaining portion of the reduced calorie fat transforms into a stable $\beta$-3 phase; and (b) the $\beta$-3 phase formed does not melt.

Certain of the present reduced calorie fats, like cocoa butter, can be crystallized into a stable $\beta$-3 phase. However, it has been found that the rate of crystallization of these reduced calorie fats into the $\beta$-3 phase is extremely slow under standard tempering conditions used with cocoa butter-based chocolate products. This rate is sufficiently slow so as to make cocoa butter-type tempering of flavored confectionary compositions containing these reduced calorie fats commercially unattractive.

Surprisingly, it has been found that tempering according to said Ehrman et al application provides a commercially attractive process that is simpler than even the standard tempering conditions used with cocoa butter-based chocolate products. In particular, this tempering process can be carried out during the normal warehousing and distribution of the flavored confectionary product. These desirable results are achieved by taking advantage of the ability of these reduced calorie fats to transform into the desired stable β-3 phase, via the less stable sub α phase. This transformation of the reduced calorie fats from the sub α phase to the stable β-3 phase according to this tempering process occurs without undesired bloom formation. The resulting tempered products also have the desired firmness and mouthmelt of cocoa butter-based chocolate products.

The present reduced calorie fats can also be fortified with vitamins and minerals, particularly the fat-soluble vitamins. U.S. Pat. No. 4,034,083 of Mattson (incorporated by reference herein) discloses polyol fatty acid polyesters fortified with fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fats-soluble vitamin well known for use in the treatment and prevention of rickets and other skeletal disorders. Vitamin D comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present reduced calorie fat material can vary. If desired, the reduced calorie fats can be fortified with a recommended daily allowance (RDA), or increment or multiple of an RDA, of any of the fat-soluble vitamins or combinations thereof.

Vitamins that are nonsoluble in fat can similarly be included in the present reduced calorie fats. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present reduced calorie fat.

The present reduced calorie fats are particularly useful in combination with particular classes of food and beverage ingredients. For example, an extra calorie reduction benefit is achieved when the fat is used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol, xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alphaaminodicarboyxlic acids and gem-diamines; and 3-hydroxy-4-alkyoxyphenyl aliphatic carboxylates or heterocyclic aromatic carboxylates.

The reduced calorie fats can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the reduced calorie fats are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Certain of the present reduced calorie fats are particularly useful in reduced calorie fat composition comprising certain substantially nonabsorbable, substantially nondigestable polyol polyesters. See. U.S. application Ser. No. 329,629 to Paul Seiden, Corey J. Kenneally, Thomas J. Wehmeier, Mary M. Fox and Raymond L. Niehoff (P&G Case 3947), filed Mar. 28, 1989, which is incorporated by reference. These reduced calorie fat compositions comprise:

a. from about 10 to about 65% of an edible, substantially nonabsorbable, substantially nondigestable polyol fatty acid polyester having at least 4 fatty acid ester groups, wherein the polyol is selected from sugars and sugar alcohols containing from 4 to 8 hydroxy groups and wherein each fatty acid group has from 2 to 24 carbon atoms; and b. from about 35 to about 90% reduced calorie triglycerides selected from MMM, MLM, MML, LLM, LML and LLL triglycerides, and mixtures thereof; wherein M is a saturated fatty acid residue selected from $C_6$ to $C_{10}$ saturated fatty acids, and mixtures thereof; wherein L is a saturated fatty acid residue selected from $C_{18}$ to $C_{24}$ saturated fatty acids, and mixtures thereof; wherein the reduced calorie triglycerides comprise: (1) at least about 85% combined MLM, MML, LLM and LML; and (2) up to about 15% combined MMM and LLL triglycerides, and wherein the fatty acid composition of the reduced calorie triglycerides comprises: (1) from about 10 to about 70% $C_6$ to $C_{10}$ saturated fatty acids; and (2) from about 30 to about 90% $C_{18}$ to $C_{24}$ saturated fatty acids.

Food products can comprise these reduced calorie fat compositions as the sole fat ingredient, or in combination with other fat ingredients such as triglyceride oils. These food products include frying oils for salted snacks and other fried foods, firm chocolate-flavored products such as chocolate-flavored candy bars or chips, as well as cooking and salad oils that are clear at room temperature, i.e., about 70° F. (21.1° C.), and preferably at lower temperatures, e.g., at about 50° F. (10° C.)

Surprisingly, certain of the present reduced calorie fats can function as anti-anal leakage agents for the polyol polyesters. In addition, the combination of the polyol polyesters with these reduced calorie fats provides significant advantages over the use of either component along. The advantages provided by these combinations include: (1) increased caloric reduction; (2) textural/taste benefits (e.g., less waxiness/greasiness, improved mouthmelt); (3) less color degradation during frying; and (4) less high temperature volatility and foaming during frying.

Bulking or bodying agents are useful in combination with the reduced calorie fats in many food combinations. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present reduced calorie fats with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, applies, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

The reduced calorie fats can also contain minor amounts of optional flavorings, emulsifiers, anti-spattering agents, anti-sticking agents, antioxidants, or the like.

Of course, judgement should be exercised to make use of appropriate reduced calorie fats and combinations of these fats with other food ingredients. For example, a combination of sweetener and fat would not be used where the specific benefits of the two are not desired. The fat and fat ingredient combinations are used where appropriate, and in the proper amounts.

Many benefits are obtained from the use of the present reduced calorie fats in food and beverage compositions, either when used alone or in combination with the ingredients discussed above. A primary benefit is the calorie reduction achieved when the fat is used as a total or partial fat replacement. This calorie reduction can be increased by using combinations of the present fats with reduced calorie sweeteners, bulking agents, or other reduced calorie of noncaloric fats. Another benefit which follows from this use is a decrease in the total amount of fats in the diet. Foods or beverages made with the reduced calorie fats instead of triglyceride fats will also contain less cholesterol, and the ingestion of these food can lead to reduced serum cholesterol and thus reduced risk of heart disease.

A related benefit is that the use of the reduced calorie fats allows the production of foods and beverages that are stable in terms of shelf stability and penetration stability. Compositions made with the reduced calorie fats have acceptable organoleptic properties, particularly taste and texture.

Dietary foods can be made with the reduced calorie fats to meet special dietary needs, for example, of person who are obese, diabetic, or hypercholesterolemic. The reduced calorie fat can be a major part of a low-fat, low-calorie, low-cholesterol diet, and they can be used alone or in combination with drug therapy or other therapy. Combinations of food or beverage products made with the reduced calorie fat can be used as part of a total dietary management regimen, based on one or more of these products, containing the reduced calorie fat alone or in combination with one or more of the above-mentioned ingredients, to provide one or more of the above-mentioned benefits.

This discussion of the reduced calorie fats uses, combinations, and benefits, is not intended to be limiting or all-inclusive. It is contemplated that other similar uses and benefits can be found that will fall within the spirit and scope of this invention.

G. Analytical Methods

1. Carbon Number Profile (CNP)

The carbon number profile (CNP) of the triglycerides (i.e. MML/MLM, MLL/LML, MMM and LLL) can be determined by programmed temperature-gas chromatography (GC) using a short fused silica column coated with methyl silicone for analysis and characterization of the composition by molecular weight. The glycerides are separated according to their respective carbon numbers, wherein the carbon number defines the total number of carbon atoms on the combined fatty acid residues. The carbon atoms on the glycerol molecule are not counted. Glycerides with the same carbon number will elute as the same peak. For example, a triglyceride composed of three $C_{16}$ (palmitic) fatty acid residues will co-elute with triglycerides made up of one $C_{14}$ (myristic), one $C_{16}$ and one $C_{18}$ (stearic) fatty acid residue or with a triglyceride composed of two $C_{14}$ fatty acid residues and one $C_{20}$ (arachidic) fatty acid residue.

Preparation of the fat sample for analysis is as follows: 1.0 ml. of a tricaprin internal standard solution (2 microg./ml.) is pipetted into a vial. The methylene chloride solvent in the standard solution is evaporated using a steam bath under a nitrogen stream. Two drops of the fat sample (20 to 40 microg.) are pipetted into a vial. If the fat sample is solid, it is melted on a steam bath and stirred well to insure a representative sample. 1.0 ml. of bis (trimethylsilyltrifluoroacetamide) (BSTFA) is pipetted into the vial which is then capped. The contents of the vial are shaken vigorously and then placed in a beating block (temperature of 100° C.) for about 5 minutes.

For determining the CNP-GC of the prepared fat samples, a Hewlett-Packard 5880A series gas chromatograph equipped with temperature programming and a hydrogen flame ionization detector is used together with a Hewlett-Packard 3351B data system. A 2 m. long, 0.22 mm. diameter fused silica capillary column coated with a thin layer of methyl silicone (Chrompak CP-SIL 5) is also used. The column is heated in an oven where temperature can be controlled and increased according to a specified pattern by the temperature programmer. The hydrogen flame ionization detector is attached to the outlet port of the column. The signal generated by the detector is amplified by an electrometer into a working input signal for the data system and recorder. The recorder prints out the gas chromatograph curve and the data system electronically integrates the area under the curve. The following instrument conditions are used with the gas chromatograph:

| Septum purge | 1 ml./min. |
|---|---|
| Inlet pressure | 5 lbs./in.$^2$ |
| Vent flow | 75 ml./min. |
| Makeup carrier | 30 ml./min. |
| Hydrogen | 30 ml./min |

| | |
|---|---|
| Air | 400 ml./min. |

1.0 microl. of the prepared fat sample is taken by a gas-tight syringe and injected into the sample port of the gas chromatograph. The components in the sample port are warmed up to a temperature of 365° C. and swept by a helium carrier gas to push the components into the column. The column temperature is initially set at 175° C. and held at this temperature for 0.5 min. The column is then heated up to a final temperature of 355° C. at a rate of 25° C./min. The column is maintained at the final temperature of 355° C. for an additional 2 min.

The chromatographic peaks generated are then identified and the peak areas measured. Peak identification is accomplished by comparison to known pure glycerides previously programmed into the data system. The peak area as determined by the data system is used to calculate the percentage of glycerides having a particular Carbon Number ($C_N$) according to the following equation:

$$\% \ C_N = (\text{Area of } C_N/S) \times 100$$

wherein S = sum of Area of $C_N$ for all peaks generated.

The Area of $C_N$ is based upon the actual response generated by the chromatograph multiplied by a response factor for glycerides of the particular Carbon Number. These response factors are determined by comparing the actual responses of a mixture of pure glycerides of various Carbon Numbers to the known amounts of each glyceride in the mixture. A glyceride generating an actual response greater than its actual amount has a response factor less than 1.0; likewise, a glyceride generating a response less than that of its actual amount has a response factor of greater than 1.0. The mixture of glycerides used (in a methylene chloride solution) is as follows:

| Component | Carbon No. | Amount (mg./ml.) |
|---|---|---|
| Palmitic acid | 16 | 0.5 |
| Monopalmitin | 16 | 0.5 |
| Monostearin | 18 | 0.5 |
| Dipalmitin | 32 | 0.5 |
| Palmitostearin | 34 | 0.5 |
| Distearin | 36 | 0.5 |
| Tripalmitin | 48 | 1.5 |
| Dipalmitostearin | 50 | 1.5 |
| Distearopalmitin | 52 | 1.5 |
| Tristearin | 54 | 1.5 |

2. Fatty Acid Profile a. Reagents and Equipment

Gas Chromatograph: HP 5890A with Flame Ionization Detector
Automatic Sampler: HP 7673A
Split Injection Part Liner: HP, Packed with glass beads
Data System: HP 3393A
Vials: 1 ml with Teflon-coated rubber-lined aluminum caps
Module Heater: Labline
Column: DB-225 30 Meters, 0.25 film thickness
Carrier Gas: Helium
BSTFA (N,O)-Bis(Trimethyl silyltrifluoroacetamide): Sigma T-1506
Fatty Acid Std.: Aldrich Reagent Grade.

b. Instrumental Conditions (flow settings)

| | |
|---|---|
| Septum purge: | 1.0 ml./min. |
| Inlet pressure: | 85 KPa |
| Split vent flow: | 35 ml./min. |
| Makeup carrier: | 31 ml./min. |
| Hydrogen: | 33 ml./min. |
| Air: | 401 ml./min. |
| Carrier flow: | 1 ml./min. | c. Sample Preparation

Pipet 1 drop (15 mg.) of sample into 1 ml. vials, add 1 ml. BSTFA, and heat to 70° C. for 15 minutes. Avoid solidification of sample prior to injection.

d. Oven Conditions

Oven temperature (initial value): 120° C.
Oven temperature (initial time): 0
Progress rate: 30° C./min.
Final valve: 220° C.
Oven temperature (post value): 220° C.
Oven temperature (final time): 20 min.
Detection temperature: 380° C.
Injection temperature: 280° C.

e. Calibration/Results

Analytical results are expressed as wt. % of total fatty acids in the sample, as determined from calibration curves for the compounds of interest. The precision of the method is ±5% as determined from reagent grade fatty acid standards.

3. Thin Layer Chromatography (TLC)

a. Reagents and Materials

Phosphomolybdic Acid (Aldrich 22, 185-6 99%)
Petroleum Ether (reagent grade)
Ethyl Ether (reagent grade)
Glacial Acetic Acid (reagent grade)
Methanol (reagent grade)
Chloroform (reagent grade)
HPTLC-GHLF 57527 Analtech TLC Plates (High Performance Thin-Layer Chromatography Plates)
Hard-layer silica coating/absorbents that fluoresce b. Procedure Dissolve 5 drops of reaction mixture in 1 ml $CHCl_3$. Use micropipet to spot 1-2 ml of solution on plate, 1.5 cm from base of plate. Wait for spot to dry and develop plate in suitable TLC chamber. Use filter paper in TLC chamber to increase solvent vapor phase. Remove plate from chamber and dry thoroughly in fume hood with an air stream. Quickly dip dried plate into 5% phosphomolybdic acid in methanol solution, making sure area of interest is submerged. Place TLC plate on hot plate set at a temperature where spots develop in 30 seconds to 1 minute. When all spots have developed, remove from hot plate and, for long term storage, either photocopy or photograph TLC plates within 2-4 hours of plate development as the developed areas will fade over time. From the origin the order of component elution is monoglyceride/glycerine, 1,2-and 2,3-glycerides, fatty acids, triglycerides (usually single spot if high MML/MLM purity), and unsaponifiable materials, e.g., soaps, etc.

c. Notes on Procedure

Plate development takes 6-8 minutes.

Plate must be dry before phosphomolybdic acid treatment or streaking will occur.

Keep solvent level in chamber below spot origin on plates.

Allow solvent front to develop to 1 cm from top of plate.

Keep TLC chamber closed or solvent system composition will change.

Mark origin and final solvent front point to calculate Rf values.

Phosphomolybdic acid solution should be prepared fresh once a month.

Development solution should be made fresh every week.

To help establish spots, run standards of known compounds to establish Rf values of the following compounds:

monoglyceride standard: monobehenin
fatty acid standard: capric or caprylic acid or behenic acid
diglyceride standard: ML or MM diglyceride
triglyceride standard: any medium or long chain saturated fatty acid triglyceride (prefer MML/MLM)

The procedure has a sensitivity of less than 0.4 wt.% relative to diglycerides spiked into the triglyceride/fatty acid matrix.

5. Free Fatty Acid Titration (as Oleic)

a. Reagents

1. Ethyl alcohol - 3A. Titrated to the phenolphthalein endpoint with 0.1N sodium hydroxide solution.
2. Sodium hydroxide - 0.1N or 0.25N.
3. Phenolphthalein - 0.5% in alcohol.

b. Apparatus

1. Balance - torsion.
2. Magnetic stirrer. Labline Magnestir, or equivalent.
3. Stirring bars. Magnetic, 0.25 in. O.D. × 1.5 in. length, Teflon-covered.
4. Buret. Digital - 25 ml., Fisher Cat. #03-840. Adapter set to fit solution bottle - Fisher Cat. #13-688-106.
5. pH meter. Beckman Expandomatic IV pH Meter.
6. Electrode. Combination - Orion Cat. #910400/Fisher Cat. #14-641-681.

c. Reference Standard

A reference standard, lauric acid (4.5 g.) dissolved in white mineral oil (1335 g.), is run with each group of samples. The results are compared with the known value for the reference standard to determine the accuracy of the sample results.

d. Titration

1. Weigh approximately 50 g. of sample into a 250 ml. Erlenmeyer flask to the nearest 0.01 g. Weigh a 15 g. sample of the lauric acid reference standard.
2. Add 50 ml. of hot neutralized 3A alcohol to the melted sample in the flask. Note: Sample should be heated only long enough to liquefy before the titration. Overheating increases the possibility of hydrolysis occurring and a consequent elevation of the free fatty acid content.
3. Add about 0.5 ml of phenolphthalein indicator to the sample.

Titrate the sample with the 0.1N NaOH solution. For light-colored samples, titrate while stirring until a very pale pink color is evident in the stirring emulsion. For dark samples, titrate until the alcohol layer, when allowed to separate, is pale pink (color should persist for at least 30 seconds). Occasionally the free fatty acid content of an apparently fresh sample is quite high. If 50 g. of sample titrates over 10 ml. with 0.1N NaOH, titrate it with 0.25N NaOH. For very high free fatty acid-glyceride mixtures, it may be necessary to weight 10 g. of sample and titrate with 0.25N NaOH.

5. Record the titration volume (T).

e. Calculation $$\% \text{ free fatty acid (as oleic)} = \frac{T \times N \times 28.2}{\text{Sample Weight (g.)}}$$

Where:
t = sample titration in ml. of NaOH
N = normality of NaOH
28.2 = milliequivalent weight of oleic acid × 100

H. Specific Examples to Illustrate MML/MLM Triglyceride-Making According to the Process of the Present Invention The following are specific examples to illustrate the making of MML/MLM triglycerides according to the process of the present invention:

EXAMPLE 1

$C_{10:0}$ (P&G C1095) fatty acid was redistilled to improve color, odor and reduce unsaponifiable levels. The $C_{10:0}$ acid was distilled at 170°-190° C. under vacuum and condensed at 40° C. An 80% middle-cut fraction of the distillate yielded a 97.5% pure $C_{10:0}$ fatty acid feedstock. $C_{8:0}$ (P&G C898) fatty acid of 97.7% purity was also used.

A series of six selective esterifications were made in a pilot plane reaction system. The reactor consisted of a hot oil heated 200 liter vessel having a variable speed agitator (3.14 cm diameter), no internal baffles, and a gas dispersion ring connected to an external nitrogen source directly below the agitator. A partial condenser consisting of a reflux column (1.96 cm diameter × 22.04 cm length) packed with metal wire mesh and a horizontal condenser was connected to the top of the reactor vessel. Total condenser capability was provided by a separate condenser/distillate trap.

Typically, about 118 kg of a mixture of $C_{10:0}$ and $C_{8:0}$ fatty acids (55:45 weight ratio) was preheated to the esterification temperature. This fatty acid mixture was used to esterify about 16.8 kg of monobehenin at a 18:1 acid to monobehenin mole ratio at esterification temperatures in the range of 174°-210° C. for 1.5 to 3.5 hours. (The monobehenin was commercially produced by molecular distillation of behenic acid/glycerol reaction products and comprised 98.1% monoglyceride, 0.5% diglyceride, 0.1% free glycerol, and 0.3% diglycerol.) The monobehenin was added incrementally as a powder over a 10 minute period to the melted fatty acids. Vigorous agitation (571 m./min. tip speed) and a nitrogen gas sparging rate of 1.4–2.1 liter/min. per liter of reaction mixture was used to remove the water generated during the esterification. The light fatty acids were refluxed by the partial condenser operated at 110° C., while generated water was condensed by the total condenser at 40° C. The esterification progress was monitored by thin layer chromatography (TLC) using high performance silica plates and a 75% petroleum ether/25% diethyl ether/1% acetic acid development solvent, followed by charring with 5% phosphomolybdic acid in anhydrous methanol. The esterification were stopped after complete elimination of diglycerides (i.e. measured level typically less than 0.4%). Composite analyses of the six esterification indicated a 6.4% MMM, 89.9% MML/MLM and 3.7% MML/LML triglyceride composition (average) in the reaction mixture. (As determined by CNP (acid free basis), "MMM"$\leq C_{24}$ to $C_{34}$, "MML/MLM"=$C_{36}$ to $C_{44}$, and "MLL/LML"$C_{46}$ to $C_{56}$.) The free fatty acid profiles for the reaction mixtures were determined to be 42.9% $C_{8:0}$, 56.2% $C_{10:0}$, 0.7% $C_{12:0}$, and 0.2% $C_{22:0}$ fatty acids (average), which suggests minimal long chain fatty acid hydrolysis occurred under these esterification conditions. (As determined by free fatty acid profiles, "long chain fatty acid"=combined $C_{20:0} C_{22:0}$ and $C_{24:0}$.)

Residual fatty acids were vacuum distilled from the reaction mixture by gradual application of vacuum. Typical residual fatty acid levels were 82% (as oleic) at the start of the distillation. The stripping temperatures ranged from 169-202° C. with vacuum levels of 2 to 50 mm Hg. Distillation was stopped when the residual fatty acids were reduced to the 5-12% level. The stripped batches were cooled to 100° C. by an external heat exchanger. Composite analyses of the six stripped batches indicated a 5.8% MMM, 90.3% MML/MLM and 3.8% MLL/LML triglyceride composition (average), which suggested excellent thermal stability for the reaction mixture. The free fatty acid profiles of the stripped batches were determined to be 1.6% $C_{8:0}$, 49.4% $C_{10:0}$, 18.8% $C_{12:0}$, 1.8% $C_{14:0}$, 0.7% $C_{16:0}$, 0.8% $C_{20:0}$, 23.9% $C_{22:0}$, and 3.1% C24:0 fatty acids (average).

The combined stripped batches were decolorized by addition of 3% Filtrol® 105 bleaching earth/0.3% Norit® 2203 activated carbon. The slurry of bleaching agents and stripped oil were heated at 75° C. for 3 hours prior to the addition of diatomaceous filter earth. The mixture was filtered through a plate and frame filter press, and yielded a clear oil. Composite analysis of bleached product indicated a 6.2% MMM, 89.8% MML/MLM and 4.0% MLL/LML triglyceride composition (average), and 11.1% free fatty acids (as oleic).

The residual fatty acids and MMM triglycerides were removed by molecular distillation on a 15 inch diameter rotor Consolidated Vacuum Corporation (CVC) still. The stripped batches were fed to the still at a 8.7 kg./hr. feed rate and a portion thereof was distilled at 17 microns pressure and a 179° C. rotor temperature. Under these conditions, a 15.8% distillate cut was made which removed all residual fatty acids and most MMM triglycerides. Composite analysis of the molecular still residue indicated a 2.0% MMM, 93.3% MML/MLM and 4.7% MLL/LML triglycerides composition (average). The level of unsaponifiables was 1.11% in the reaction mixture.

The residue from the first distillation was passed through a second CVC molecular still to separate the desired MLL/MLM triglycerides from the MLL/LML triglycerides and residual color/unsaponifiables. A feed rate of 10.5 kg./hr. and a 191° C. rotor temperature at 16 microns pressure was used to distill off the desired MML/MLM triglycerides. A 45% cut was taken on the first pass, followed by a 26% cut on the second pass. Composite analyses of the distillates indicated a 2.9% MMM, 96.5% MML/MLM and 0.6% MML/LML triglyceride composition (average). The level of unsaponifiables was 0.25% in the distilled product which suggested good separation of these components by molecular distillation.

The distilled MML/MLM triglycerides were clear in color, odor-free and bland in taste. Follow-up evaluations in chocolate-flavored products indicated good utility as a cocoa butter replacer. Overall yield of purified MML/MLM triglycerides was 56% based on the initial amount of monobehenin.

EXAMPLE 2

$C_{8:0}$ (P&G C895) and $C_{10:0}$ (P&G C1095) fatty acids having 95% purity were redistilled to remove color, odor and reduce unsaponafiable levels. Approximately 480 grams of the respective acid was placed in a 1 liter three-necked round bottom flask. Heat was applied by a thermostatically controlled heating mantle. The acids were condensed by a cold trap into a receiving flask. About 80% of the respective acid was distilled, yielding 98.6% pure $C_{8:0}$ and 97.1% pure $C_{10:0}$ fatty acid feedstocks.

Fifty grams of monobehenin (commercially produced by molecular distillation of a behenic acid/glycerol reaction product feed) was esterified using an 18:1 acid to monobehenin mole ratio at a temperature of 220° C. for 80 minutes. The fatty acids were added on an equal mole basis (55% $C_{10:0}$/45% $C_{8:0}$). The monobehenin contained 95.8% monoglyceride, 2.6% diglyceride, and 0.36% glycerol. Progress of the esterification was monitored by TLC using the procedure described in Example 1.

Excess fatty acids were vacuum distilled from the reaction vessel using a cold water condenser and collection trap. The initial free fatty acid level of the completed esterification was 82% (as $C_{10:0}$ fatty acid). Over a 30 minute period, free fatty acid was reduced to 4.1% by heating the reaction mixture at 115°-150° C. using a 0.25-1 mm Hg vacuum. A final residual fatty acid level of 1.8% was obtained by an additional 30 minutes of stripping at 200° C. using a 1 mm Hg vacuum.

The overall synthesis yield of the MML/MLM triglycerides was 92.7% (calculated on the basis of the starting monobehenin purity). Key compositional data were as follows:

|  | After Esterification | After Acid Removal |
|---|---|---|
| Fatty Acid (% as $C_{10:0}$) | 82 | 1.8 |
| Glyceride Composition* |  |  |
| MMM (%) | 10.5 | 9.9 |
| MML/MLM (%) | 88.8 | 87.4 |
| MLL/LML (%) | 1.4 | 2.7 |
| ML(OH) (%) | 1.1 | — |
| Fatty Acid Profile |  |  |
| $C_{8:0}$ | 45.7 | — |
| $C_{10:0}$ | 53.4 | 31.6 |
| $C_{12:0}$ | 0.4 | 6.2 |
| $C_{14:0}$ | — | 3.8 |
| $C_{20:0}$ | — | 1.2 |
| $C_{22:0}$ | 0.4 | 41.4 |
| $C_{24:0}$ | 0.2 | 17.0 |

*By CNP (acid free basis) "MMM" = $C_{24}$ to $C_{34}$, "ML(OH)" = $C_{30}$ to $C_{32}$, "MML/MLM" = $C_{36}$ to $C_{44}$, "MLL/LML" = $C_{46}$ to $C_{56}$ The acid stripped mixture was fractionally crystallized by first dissolving 49 grams of it in 500 ml. of ethanol (absolute) at 45° C. The solution was allowed to slowly cool to 25° C. and an 8.5% MLL/LML fraction was filtered off on Whatman #4 filter paper using a Buchner funnel. The filtrate was cooled to −4° C. using an ice bath, followed by filtration of a 11.5% MMM/free fatty acid fraction. The residual solvent was removed by nitrogen gas stripping on a steam bath, yielding 39 grams of high purity MML/MLM triglycerides. Carbon number profiles (CNP) indicated a 5% MMM, 93.3% MML/MLM and 1.7% MLL/LML triglyceride composition. Overall yield of purified MML/MLM triglycerides was 74% based on the starting amount of monobehenin.

EXAMPLE 3

High purity (98.2% pure) monostearin obtained by multiple hexane crystallization of crude monostearin (stearyl chloride reacted with glycerol acetone, followed by acid hydrolysis) was esterified with reagent grade (99% pure) $C_{8:0}$ and $C_{10:0}$ fatty acids to determine the effects of esterification temperature and mole ratio of acid to monostearin on MML/MLM triglyceride purity.

Approximately 50 grams of monostearin was placed in a 250 ml. three-necked round bottom flask and melted with the appropriate amount of $C_{10:0}$ fatty acid or a $C_{8:0}/C_{10:0}$ (45:55 weight ratio) fatty acid mixture. Temperature control was provided by a thermostatically controlled heating mantle. The heated mixture was agitated vigorously with a magnetic stirrer. Gaseous nitrogen was bubbled through the reaction mixture at the rate of 0.8 l./min. by a gas dispersion tube and flowmeter. A reflux condenser operated at 110° C. allowed displacement of generated water vapor to a 22° C. total condenser and trap. Progress of the esterification was monitored by TLC according to the procedure described in Example 1.

Several runs were made as shown below:

| | Example 3 | | | | |
|---|---|---|---|---|---|
| | Run | | | | |
| | A | B | C | D | E |
| Fatty Acid | $C_{10:0}$ | $C_{10:0}$ | $C_{10:0}$ | $C_{10:0}$ | $C_{10:0}/C_{8:0}$ |
| Esterification temperature (°C.) | 260 | 180 | 180 | 180 | 180 |
| Acid to mono-stearin mole ratio | 2.2:1 | 2.2:1 | 4.4:1 | 8.8:1 | 18:1 |

| | Example 3 | | | | |
|---|---|---|---|---|---|
| | Run | | | | |
| | A | B | C | D | E |
| Glyceride Composition of product* | | | | | |
| MMM (%) | 6.4 | 17.7 | 15.8 | 15.1 | 5.2 |
| MML/MLM (%) | 38.2 | 57.8 | 69.9 | 77.3 | 93.2 |
| MLL/LML (%) | 40.3 | 23.3 | 13.8 | 7.4 | 1.6 |
| LLL (%) | 14.6 | 1.7 | 0.5 | 0.2 | — |
| ML(OH) (%) | 0.5 | 0.4 | — | — | — |

*By CNP (acid free basis) "MMM" = $C_{24}$ to $C_{30}$; "ML(OH)" = $C_{26}$ to $C_{28}$; "MML/MLM" = $C_{32}$ to $C_{40}$; "MLL/LML" = $C_{42}$ to $C_{48}$; "LLL" = $C_{50}$ or higher

EXAMPLE 4

Monobehenin was esterified with a mixture of reagent grade (99% pure) $C_{8:0}$ and $C_{10:0}$ fatty acids (45:55 weight ratio) to determine the effects of esterification temperature and mole ratio of acids to monobehenin on MML/MLM triglyceride purity.

USP grade glycerol behenate (20% monobehenin content) was solubilized in 9.3 parts absolute ethanol over a steam bath. The resultant mixture was allowed to crystallize at 32° C. for 5 days prior to filtration of the diglyceride/triglyceride fraction. Water was added to provide a 90% ethanol solution prior to crystallization for 1 week at 4° C. to remove residual glycerol. The solution was cooled to −10° C. prior to filtration. The recovered monobehenin was vacuum dried overnight at 50° C., yielding 84% pure monobehenin.

About 70 grams of the purified monobehenin was dissolved in 250 grams absolute ethanol over steam. The mixture was cooled to 25° C. by ice water prior to filtration of diglycerides. This procedure was repeated at 19° C., prior to rotovap concentration of the second filtrate. The resultant monobehenin was 98.7% pure with 1.3% diglycerides. Residual ethanol was removed by vacuum drying at 50° C.

The monobehenin was esterified with the mixture of $C_{8:0}$ and $C_{10:0}$ fatty acids (45:55 weight ratio) using the synthesis procedure of Example 3. The results of several runs at varying acid to monobehenin mole ratios and esterification temperatures are shown as follows:

| | Example 4 | | | | | | | |
|---|---|---|---|---|---|---|---|---|
| | Run | | | | | | | |
| | F | G | H | I | J | K | L | M |
| Esterification temperature (°C.) | 110 | 140 | 140 | 180 | 180 | 220 | 220 | 250 |
| Acid to monobehenin mole ratio | 8.8:1 | 8.8:1 | 18:1 | 8.8:1 | 18:1 | 18:1 | 27:1 | 18:1 |
| Glyceride composition of product* | | | | | | | | |
| MMM (%) | 13.4 | 7.6 | 5.7 | 6.8 | 5.0 | 6.2 | 4.6 | 8.3 |
| MML/MLM (%) | 67.7 | 80.5 | 87.5 | 84.0 | 89.5 | 89.5 | 91.5 | 87.2 |
| MLL/LML (%) | 13.5 | 10.4 | 5.6 | 8.1 | 4.0 | 3.2 | 2.7 | 2.9 |
| LLL (%) | 0.4 | 0.2 | — | 0.1 | — | — | — | — |
| ML(OH) (%) | 5.0 | 1.3 | 1.2 | 1.0 | 1.5 | 1.1 | 1.2 | 1.6 |
| Reaction time (Hr) | 69 | 20 | 20 | 3.5 | 2 | 1 | 1 | 0.6 |
| Acid hydrolysis (%)** | 2.2 | 1.7 | 1.6 | — | 1.6 | 0.8 | 1.2 | 6.3 |

*By CNP (acid free basis) "MMM" = $C_{24}$ to $C_{34}$; "ML(OH)" = $C_{30}$ to $C_{32}$; "MML/MLM" = $C_{36}$ to $C_{44}$; "MLL/LML" = $C_{46}$ to $C_{56}$; "LLL" = $C_{58}$ or higher
**combined $C_{20:0}$, $C_{22:0}$ and $C_{24:0}$

EXAMPLE 5

Monobehenin (Mono) having various levels of impurities such as glycerol (Gly) and $C_{22:0}$ diglycerides (Digly) was esterified with a mixture of reagent grade (99% pure) $C_{8:0}$ and $C_{10:0}$ fatty acids (45:55 weight ratio) by the synthesis procedure of Example 3. The monobehenin was prepared by either ethanol fractional crystallization or molecular distillation of crude behenic acid/glycerol reaction products.

The results of several esterification runs are shown below:

|     | Monobehenin Purity | | | Esterification | Example 5 Acid to Monobehenin | Glyceride Composition of Product* | | | | |
|---|---|---|---|---|---|---|---|---|---|---|
| Run | Mono (%) | Gly (%) | Digly (%) | Temperature (°C.) | Mole Ratio (#) | MMM (%) | MML/MLM (%) | MLL/LML (%) | LLL (%) | ML(OH) (%) |
| N | 94.0 | 5.4 | 0.6 | 260 | 2.2 | 36.0 | 42.2 | 19.5 | 2.3 | — |
| O | 94.0 | 5.4 | 0.6 | 180 | 8.8 | 26.3 | 66.5 | 7.2 | — | — |
| P | 86.4 | — | 13.6 | 180 | 4.4 | 12.3 | 65.3 | 20.6 | 1.0 | 0.8 |
| Q | 86.4 | — | 13.6 | 180 | 8.8 | 9.1 | 71.3 | 18.1 | 0.6 | 0.9 |
| R | 94.5 | — | 5.5 | 180 | 8.8 | 5.4 | 80.9 | 12.6 | 0.2 | 0.9 |
| S | 95.8 | 0.4 | 2.6 | 180 | 8.8 | 8.7 | 83.9 | 5.8 | 0.1 | 1.5 |
| T | 98.1 | 0.1 | 1.3 | 180 | 8.8 | 6.8 | 84.0 | 8.1 | 0.1 | 1.0 |
| V | 98.1 | 0.1 | 1.3 | 180 | 18.0 | 4.9 | 89.5 | 4.1 | — | 1.5 |

*By CNP, as in Example 4

EXAMPLE 6

The benefit of adding monoglyceride sequentially during the esterification was evaluated using high purity (98.6% monoglyceride, 0.3% glycerol) monobehenin commercially produced by molecular distillation of a crude behenic acid/glycerol reaction mixture. During each esterification, the monobehenin was added to a melted mixture of reagent grade (99% pure) $C_{8:0}$ and $C_{10:0}$ fatty acids (45:55 weight ratio), followed by heating to 200° C. using the procedure described in Example 3. The total acid to monobehenin mole ratio for each esterification was 18:1. The Control esterification was completed in 1.5 hours as determined by TLC monitoring. The sequential addition run involved adding monobehenin in five equal parts as a powder to the melted fatty acids at 200° C. Approximately 1.75 hours were required for complete conversion of diglycerides (i.e., measured level less than 0.4%) to triglyceride products.

The results are shown below:

| | Control | Sequential |
|---|---|---|
| Glyceride composition of product* | | |
| MMM (%) | 10.7 | 7.9 |
| MML/MLM (%) | 88.6 | 91.6 |
| MLL/LML (%) | 0.7 | 0.5 |

*By CNP, as in Example 2.

EXAMPLE 7

The importance of removing water generated during esterification was evaluated. In this evaluation, a mixture of reagent grade (99% pure) $C_{8:0}$ and $C_{10:0}$ fatty acids (45:55 weight ratio) was reacted with commercially produced molecularly distilled monobehenin (98.1% monoglyceride, 0.5% diglycerides, 0.1% glycerol, and 0.3% diglycerol monoglyceride) at 200°–220° C. and at an acid to monobehenin mole ratio of 18:1. The esterification were conducted in a 2 liter three-necked round bottom flask. Esterification temperature was controlled by a heating mantle and thermowatch. A 1.18 cm. diameter agitator was connected to a variable speed drive and controller. Gaseous nitrogen was flow controlled and introduced by a sparge tube next to the agitator. A reflux container operated at 110° C. allowed displacement of generated water vapor to a 22° C. total condenser and trap. A series of runs were made under various water removal conditions to determine the effects of vacuum, nitrogen sparge rate, degree of agitation, and the use of adsorbents (3A molecular sieves, Fisher M564-550). The esterifications were monitored by TLC, and terminated upon reaction of all diglycerides (i.e., measured level less than 0.4%). The results of these runs are shown below:

| | | Example 7 | | | | | |
|---|---|---|---|---|---|---|---|
| Run | Pressure (mm Hg) | Sparge Rate (L/Min-L) | Tip Speed (ft./min.) | Triglyceride Composition of Product (%)* | | | Acid Hydrolysis (%)** |
| | | | | MMM | MML/MLM | MLL/LML | |
| I | 760 | 1.6 | 51.1 | 7.3 | 87.9 | 4.9 | 5.2 |
| II | 760 | 16 | 127.6 | 5.0 | 89.3 | 5.8 | 2.1 |
| III | 760 | 1.6 | none | 7.3 | 87.7 | 5.0 | 7.8 |
| IV | 760 | none | none | 22.7 | 72.4 | 4.9 | 28.0 |
| V | 145 | none | none | 4.9 | 90.5 | 4.7 | 2.5 |
| VI*** | 760 | none | 51.1 | 7.8 | 86.2 | 6.0 | — |

*By CNP, as in Example 2
**Combined $C_{20:0}$, $C_{22:0}$ and $C_{24:0}$
***3 A molecular sieves (50 g. per liter of reaction mixture)

EXAMPLE 8

The effect of strong acid catalyst on selective esterification of monoglycerides was evaluated using phosphoric acid and p-toluenesulfonic acid catalysts. In this evaluation, monobehenin (98.1% pure) commercially produced by molecular distillation of a behenic acid/glycerol reaction product feed was esterified at varying fatty acid to monoglyceride mole ratios at 180° C. Reagent grade phosphoric acid (85% solution) and p-toluenesulfonic acid catalysts were added at 0.4% of the reaction mixture. The catalysts were added after the monobehenin-$C_{8:0}/C_{10:0}$ fatty acid reaction mixture had reached 110° C. The esterification procedure previously described in Example 3 was used in this experiment. Progress of the esterification was monitored by TLC, and was terminated upon conversion of all diglycerides (i.e., measured level less than 0.4%) to product.

The result of these experiments are shown below:

| | | Example 8 | | | |
|---|---|---|---|---|---|
| | Acid to Monobehenin | Triglyceride Composition of Product (%)* | | | Acid Hydrolysis |
| Catalyst | Mole Ratio | MMM | MML/MLM | MLL/LML | LLL | (%)** |
| None | 18:1 | 6.4 | 89.5 | 4.0 | — | 2.0 |
| $H_3PO_4$ | 2.3:1 | 20.9 | 48.4 | 26.7 | 4 | 59.2 |
| p-toluenesulfonic | 3:1 | 25.1 | 40.1 | 29.1 | 5.8 | 11.7 |
| p-toluenesulfonic | 18:1 | 15.9 | 62.7 | 21.4 | — | 6.9 |

*By CNP, as in Example 4
**Combined $C_{20:0}$, $C_{22:0}$ and $C_{24:0}$

What is claimed is:

1. A process for selectively making MML/MLM triglycerides, wherein M is a $C_6$-$C_{10}$ fatty acid residue or mixture thereof and L is a $C_{18}$-$C_{24}$ fatty acid residue or mixture thereof, said process comprising the step of esterifying an at least about 60% pure $C_{18}$-$C_{24}$ fatty acid monoglyceride or mixture thereof with an at least about 90% pure $C_6$-$C_{10}$ fatty acid or mixture thereof at a temperature of from about 140° to about 250° C. in the absence of an esterification catalyst, wherein the mole ratio of fatty acid to monoglyceride is at least about 3:1, and wherein water generated during said esterification step is continuously removed.

2. The process of claim 1 wherein the monoglyceride is at least about 90% pure $C_{18}$-$C_{24}$ saturated fatty acid monoglyceride or mixture thereof, and wherein the fatty acid is at least about 90% pure $C_6$-$C_{10}$ saturated fatty acid or mixture thereof.

3. The process of claim 2 wherein said esterification step is carried out in a solvent-free system.

4. The process of claim 3 wherein the monoglyceride is at least about 95% pure, with about 3% or less LL diglycerides, about 1% or less glycerol and about 1% or less glycerol dehydration products.

5. The process of claim 4 wherein the fatty acid is at least about 95% pure.

6. The process of claim 5 wherein the mole ratio of fatty acid to monoglyceride is from about 4:1 to about 36:1.

7. The process of claim 6 wherein the mole ratio of fatty acid to monoglyceride is from about 8:1 to about 20:1.

8. The process of claim 4 wherein said esterification step is carried out at a temperature off rom about 180° to about 220° C.

9. The process of claim 8 wherein said esterification step is carried out for from about 0.1 to about 7 hours.

10. The process of claim 9 wherein said esterification step is carried out for from about 1 to about 5 hours.

11. The process of claim 9 wherein water generated during said esterification step is continuously removed by inert gas sparging under conditions of high shear mixing, by vacuum distillation, or by a combination thereof.

12. The process of claim 9 wherein water generated during said esterification step is continuously removed by adsorption with a hydrophilic material selected from the group consisting of zeolite molecular sieves, activated carbon and activated alumina.

13. The process of claim 12 wherein the level of MML/MLM triglycerides is at least about 80% and wherein the level of diglycerides is about 1% or less after said esterification step.

14. The process of claim 13 which comprises the further steps of bleaching the MML/MLM triglycerides, followed by deodorizing the bleached MML/MLM triglycerides.

15. The process of claim 13 comprising the further step of purifying the MML/MLM triglycerides obtained after said esterification step to decrease the level of fatty acids to about 0.5% or less, the level of MMM triglycerides to about 3% or less and the level of MLL/LML triglycerides to about 3% or less.

16. The process of claim 15 wherein said purification step includes a molecular distillation step to separate the fatty acids and MMM triglycerides as the distillate fraction from the MML/MLM and MLL/LML triglycerides.

17. The process of claim 16 wherein said purification step includes a second molecular distillation step to separate the MML/MLM triglycerides as the distillate fraction from the MLL/LML triglycerides.

18. The process of claim 3 wherein the fatty acid is melted prior to said esterification step and wherein the monoglyceride is added slowly to the melted fatty acid at a controlled rate of addition during said esterification step such that the level of unreacted monoglyceride is about 0.2% or less.

19. A solvent-free process for selectively making MML/MLM triglycerides, wherein M is a $C_8$ saturated fatty acid residue, a $C_{10}$ saturated fatty acid residue, or mixture thereof, and L is at least about 90% behenic fatty acid residues, said process comprising the step of esterifying an at least about 90% pure monobehenin monoglyceride, with an at least about 90% pure $C_8$ saturated fatty acid, $C_{10}$ saturated fatty acid, or mixture thereof, at a temperature of from about 180° to about 220° C. for from about 0.1 to about 7 hours in the absence of an esterification catalyst, wherein the mole ratio of the fatty acid to monoglyceride is from about 8:1 to about 20:1 and wherein water generated during said esterification step is continuously removed.

20. The process of claim 19 wherein the fatty acid is at least about 90% pure $C_8$ saturated fatty acid.

21. The process of claim 19 wherein the fatty acid is at least about 90% pure $C_{10}$ saturated fatty acid.

22. The process of claim 19 wherein the weight ratio of $C_8$ to $C_{10}$ saturated fatty acids is from about 30:70 to about 45:55.

23. The process of claim 19 wherein the fatty acid is at least about 95% pure.

24. The process of claim 23 wherein the monobehenin monoglyceride is at least about 95% pure, with about 3% or less LL diglycerides, about 1% or less glycerol and about 1% or less glycerol dehydration products.

25. The process of claim 24 wherein water generated during said esterification step is continuously removed by inert gas sparging under conditions of high shear mixing, by vacuum distillation, or by a combination thereof.

26. The process of claim 24 wherein water generated during said esterification step is continuously removed by adsorption with a hydrophilic material selected from the group consisting of zeolite molecular sieves, activated carbon and activated alumina.

27. The process of claim 24 wherein the level of MML/MLM triglyceride is from about 80 to about 96% and wherein the level of diglycerides is about 1% or less after said esterification step.

28. The process of claim 27 which comprises the further steps of bleaching the MML/MLM triglycerides, followed by deodorizing the bleached MML/MLM triglycerides.

29. The process of claim 27 comprising the further step of purifying the MML/MLM triglycerides obtained after said esterification step to decrease the level of fatty acids to about 0.5% or less, the level of MMM triglycerides to about 3% or less and the level of MLL/LML triglycerides to about 3% or less.

30. The process of claim 28 wherein said purification step includes a molecular distillation step to separate the fatty acids and MMM triglycerides as the distillate fraction from the MML/MLM and MLL/LML triglycerides.

31. The process of claim 30 wherein said purification step includes a second molecular distillation step to separate the MML/MLM triglycerides as the distillate fraction from the MLL/LML triglycerides.

32. The process of claim 19 wherein the fatty acid is melted prior to said esterification step and wherein the monobehenin monoglyceride is added slowly to the melted fatty acid at a controlled rate of addition during said esterification step such that the level of unreacted monoglyceride is about 0.2% or less.

33. The process of claim 19 wherein said esterification step is carried out for from about 1 to about 5 hours.

34. The process of claim 3 wherein the monoglyceride is at least about 90% pure $C_{20}$–$C_{24}$ saturated fatty acid monoglyceride or mixture thereof.

* * * * *

UNITED STATES PATENT AND TRADEMARK OFFICE
CERTIFICATE OF CORRECTION

Page 1 of 2

PATENT NO. : 5,142,071

DATED : August 25, 1992

INVENTOR(S) : Bernard W. Kluesener; Gordon K. Stipp David K. Yang

It is certified that error appears in the above-identified patent and that said Letters Patent is hereby corrected as shown below:

Col. 1, line 26, "triglycerides" should be --triglyceride--
Col. 2, line 27, "undesirably" should be -- undesirable --
Col. 3, line 60, "high" should be -- highly --
Col. 7, line 5, "and particularly," should be -- and, particularly, --;
Col. 7, line 8, insert a comma after "settling";
Col. 7, line 11, "desirably" should be -- desirable --;
Col. 7, line 32, insert "D." before "Esterification."
Col. 8, line 23, "25°C" should be -- 250°C --;
Col. 8, line 41, "$C_8C_{10}$" should be $C_8/C_{10}$ --.
Col. 9, line 10, "configuration" should be -- configurations -- .
Col. 11, line 25, "in an " should be -- in any -- ;
Col. 11, line 31, "high" should be -- highly -- ;
Col. 11, line 48, "good" should be -- goods --.
Col. 12, line 6, "enhancer" should be -- enhancing -- .
Col. 13, line 21, "fats-soluble" should be -- fat-soluble --.
Col. 13, line 35, "material" should be -- materials -- .
Col. 14, line 14, "composition" should be -- compositions -- ;
Col. 14, line 59, "along" should be -- alone -- .
Col. 15, line 23, "applies" should be -- apples -- ;
Col. 15, line 54, "food" should be -- foods -- ;
Col. 15, lines 63 and 64, "person" should be -- persons -- .
Col. 21, line 10, "esterification" should be -- esterifications -- ;
Col. 21, line 14, the symbol preceding "$C_{24}$" should be -- = -- ;

UNITED STATES PATENT AND TRADEMARK OFFICE
CERTIFICATE OF CORRECTION

PATENT NO. : 5,142,071
DATED : August 25, 1992
INVENTOR(S) : Bernard W. Kluesener, et. al.

It is certified that error appears in the above-indentified patent and that said Letters Patent is hereby corrected as shown below:

Col. 27, line 60, "off rom" should be -- of from --.

Signed and Sealed this

Eleventh Day of January, 1994

Attest:

BRUCE LEHMAN

Attesting Officer       Commissioner of Patents and Trademarks